US008126246B2

(12) United States Patent
Farrer et al.

(10) Patent No.: US 8,126,246 B2
(45) Date of Patent: Feb. 28, 2012

(54) SYSTEMS AND METHODS FOR MEASURING SURFACE SHAPE

(75) Inventors: Stephen W. Farrer, Albuquerque, NM (US); James Copland, Albuquerque, NM (US); Thomas D. Raymond, Edgewood, NM (US); Wei Xiong, Albuquerque, NM (US)

(73) Assignee: AMO Wavefront Sciences, LLC, Santa Ana, CA (US)

( * ) Notice: Subject to any disclaimer, the term of this patent is extended or adjusted under 35 U.S.C. 154(b) by 551 days.

(21) Appl. No.: 12/350,895

(22) Filed: Jan. 8, 2009

(65) Prior Publication Data

US 2009/0175525 A1 Jul. 9, 2009

Related U.S. Application Data

(60) Provisional application No. 61/019,807, filed on Jan. 8, 2008, provisional application No. 61/114,978, filed on Nov. 14, 2008.

(51) Int. Cl.
*G06K 9/00* (2006.01)
(52) U.S. Cl. ........................................ 382/131; 382/141
(58) Field of Classification Search .................. 382/131, 382/141; 351/212, 205, 206, 211, 247; 356/614, 356/625; 606/3, 4, 5
See application file for complete search history.

(56) References Cited

U.S. PATENT DOCUMENTS

| 5,054,907 A | 10/1991 | Sklar et al. |
| 5,116,115 A | 5/1992 | Lange et al. |
| 5,159,361 A | 10/1992 | Cambier et al. |
| 5,208,619 A * | 5/1993 | Campbell ...................... 351/211 |
| 5,777,718 A | 7/1998 | Kohayakawa |
| 5,965,330 A * | 10/1999 | Evans et al. .................... 430/321 |
| 5,986,745 A * | 11/1999 | Hermary et al. ............. 356/3.03 |
| 6,052,180 A | 4/2000 | Neal et al. |
| 6,059,773 A * | 5/2000 | Maloney et al. ................... 606/4 |
| 6,120,150 A * | 9/2000 | Sarver et al. .................. 351/247 |
| 6,130,419 A | 10/2000 | Neal |
| 6,467,907 B1* | 10/2002 | Fujieda et al. ................ 351/212 |
| 6,548,797 B1 | 4/2003 | Ai |
| 6,550,917 B1 | 4/2003 | Neal et al. |
| 6,572,230 B2* | 6/2003 | Levine .......................... 351/221 |
| 6,634,750 B2 | 10/2003 | Neal et al. |
| 6,751,344 B1 | 6/2004 | Grumbine |
| 7,219,998 B2* | 5/2007 | Grove et al. ................... 351/212 |
| 7,436,520 B1 | 10/2008 | Doerband |
| 7,491,350 B2* | 2/2009 | Silvestrini ...................... 264/1.1 |
| 7,623,251 B2* | 11/2009 | Neal et al. ...................... 356/625 |
| 7,648,241 B2* | 1/2010 | Bentley et al. ................ 351/214 |
| 7,976,163 B2* | 7/2011 | Campbell et al. ............. 351/212 |

OTHER PUBLICATIONS

Victor Arni D.P. Sicam, PhD, "Pseudo Forward Ray-Tracing: A New Method for Surface Validation in Cornea Topography", Optometry and Vision Science, vol. 84, No. 9, Sep. 2007 pp. E915-E923.

* cited by examiner

*Primary Examiner* — Sang Nguyen
(74) *Attorney, Agent, or Firm* — AMO Wavefront Sciences, LLC.

(57) ABSTRACT

A system for determining a surface shape of a test object includes a pattern having a plurality of first elements dispose about a central axis and defining an aperture containing the central axis. The first elements includes a plurality of common elements having a common form and a reference element having a reference form that is different than the common form. The system further comprises a detector array and an optical system. The optical system is adapted to provide an image of the first elements when light reflects off a surface of a test object, passes through the aperture, and is received by the detector array. The reference form may be configured to facilitate an association between the common elements and the spot images of the common elements.

23 Claims, 6 Drawing Sheets

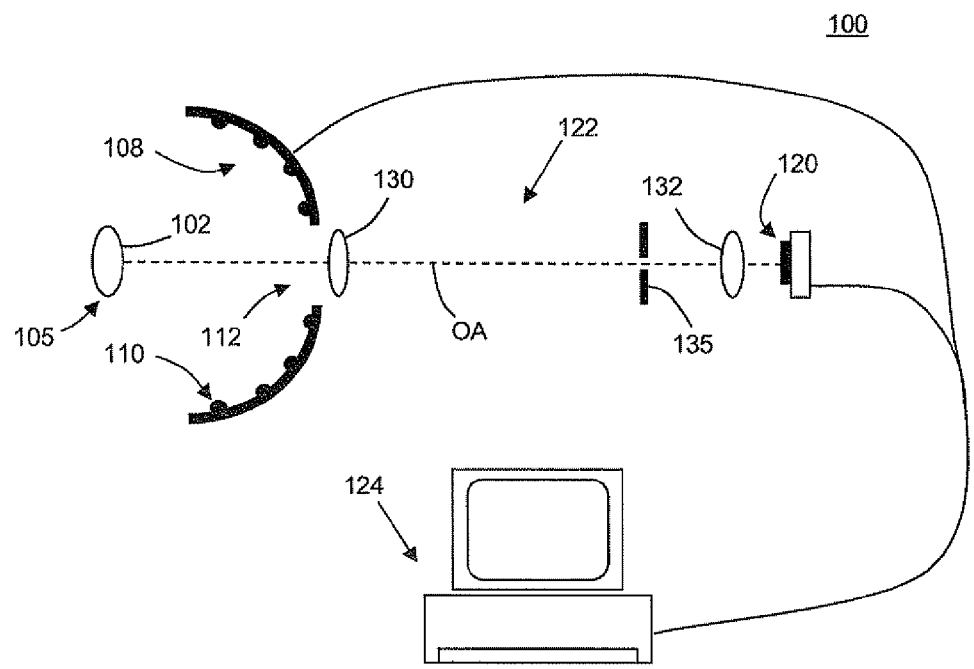
FIG. 1
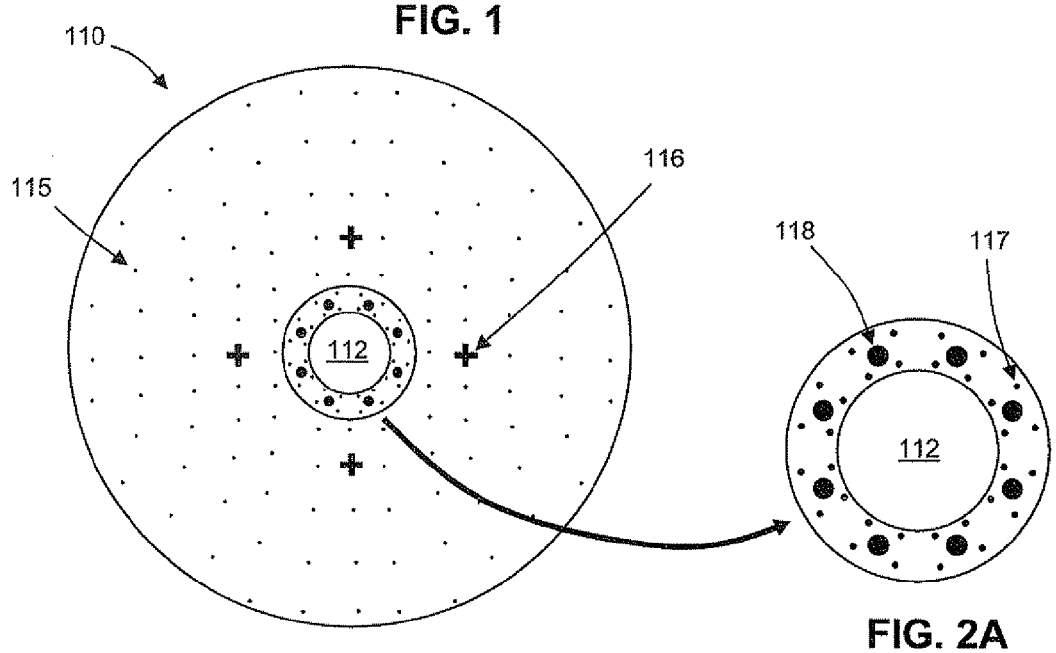
FIG. 2
FIG. 2A

SYSTEMS AND METHODS FOR MEASURING SURFACE SHAPE

RELATED APPLICATION

This application claims priority to U.S. provisional application No. 61/019,807 filed on Jan. 8, 2008, and to U.S. provisional application No. 61/114,978, filed on Nov. 14, 2008, the entire contents of each of which applications are hereby incorporated by reference in their entirety for all purposes as if fully set forth herein.

BACKGROUND OF THE INVENTION

1. Field of the Invention

The current invention relates generally to optical systems and methods for non-contact examination of objects, and more specifically to optical systems and methods for determining surface profiles or shapes of a test object.

2. Description of the Related Art

The surface shape of an object under test may be obtained through the use of non-intrusive optical diagnostic methodologies. For example, the wavefront produced by light reflected from the surface of a test object may be propagated to a wavefront analyzer such as a Shack-Hartmann wavefront sensor, where the measured shape of the imaged wavefront may be correlated to the surface profile of the object under test. Alternatively, a mask or pattern, such as that produced by a series of Placido rings or Placido-type sources, may be reflected off the test object and re-imaged at a detector. In such systems the surface of the test object may be considered as part of an optical system, so that deviations of the resulting image from an ideal may be used to infer or determine the shape of the test object.

One commercial use of Placido-type sources has been in the measurement of the shape of corneal surfaces of animal and human subjects, for example, in order to provide a custom treatment plan prior to a corneal refractive procedure such as LASIK or PRK. Since a large portion of aberrations produced by an eye typically are generated by the front surface of the cornea, corneal topography can be utilized to provide improved visual outcomes. However, other aberrations can be produced by other portions of the eye, such as the back surface of the cornea, the natural lens, the vitreous humor, a previously implanted intraocular lens, and the like. As a consequence other types of diagnostic instrumentation have been developed such as pachymeters, optical coherence tomography (OCT) sensors, and wavefront sensors, and the like. Such systems may be combined with corneal topographers to provide a more complete analysis of ocular aberrations and to provide treatments resulting in better refractive outcomes. Furthermore, in some systems, the combination of elements can improve the accuracy or fidelity of a given measurement system. For example, the addition of corneal topography information to a system for whole eye wavefront measurement may be useful, not only in understanding the optical system (such as the eye), but in producing better and more accurate information.

In a general sense, Placido-type systems utilize a mapping of points or shapes of a mask or pattern to an image or detector plane in order to deduce what test object shape is responsible for the observed mapping. Such a mapping can become more difficult for complex test object shapes and/or when a highly resolved or high frequency surface features are desired. For example, adjacent points or zones on a topographer mask or pattern may be mapped to very different points or zones in an image or detector plane due to the presence of large curvature gradients on the reflective test object. Corneal surfaces may include such complex forms and thus currently available corneal topographers may have limited accuracy in some cases.

Accordingly, there is a need for measurement systems and methods that are able to provide more accurate surface measurements for relatively complex surfaces, such as those found in corneal topography.

BRIEF DESCRIPTION OF THE DRAWINGS

Embodiments of the present invention may be better understood from the following detailed description when read in conjunction with the accompanying drawings. Such embodiments, which are for illustrative purposes only, depict novel and non-obvious aspects of the invention. The drawings include the following figures:

FIG. 1 is a schematic drawing of a measurement system according to an embodiment of the present invention.

FIG. 2 is a front view of pattern of elements used in the system in FIG. 1.

FIG. 2A is a magnified view of a portion of the pattern of elements shown in FIG. 2.

DETAILED DESCRIPTION OF THE DRAWINGS

Figure 3:
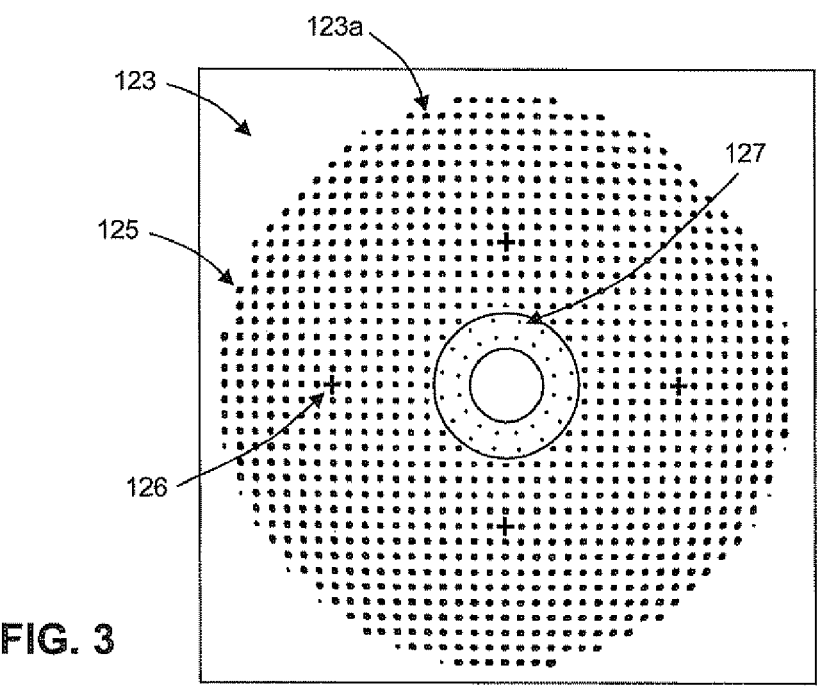
FIG. 3 is a view of an image produced of the pattern of elements of the system shown in FIG. 1.

Embodiments of the present invention are directed to devices, systems, and methods for determining the shape or profile of a surface of an object. In certain embodiments, the surface measurement may be combined with other optical diagnostic methodologies for determining optical and physical characteristics of an object. Embodiments of the present invention find particular use in ophthalmic application such as for characterizing or measuring corneal profiles and aberrations. In such embodiments, the surface measurement may be enhanced by combination with other types of measurements, such as wavefront analyzer, corneal tomographer (e.g., OCT), or the like.

Embodiments of the present invention may find particular use in measuring the profiles of more complex surfaces previously not possible with related prior art systems, or in providing greater accuracy for such measurements than has been attainable with such prior art systems. In addition, other types of optical systems may benefit from embodiments of the present invention, including optical measurement of contact lenses, molds for contact lenses, intraocular lenses (IOLs), molds for IOLs, spectacle lens, and/or molds or spectacle lens blanks. Furthermore, there are many other types of optical elements that may benefit, such as telescope mirrors, camera or imaging optics, microscope objectives, glass, wafers, or other substrates, and many other types of elements.

Referring to FIG. 1, a system 100 for determining a shape of a surface 102 of a test object 105 is illustrated that is according to an embodiment of the present invention. The system 100 comprises a pattern 108 including a plurality of first elements 110 dispose about a central axis OA. The pattern 108 defines an aperture 112 containing the central axis OA. With additional reference to FIG. 2, the first elements 110 include a plurality of common elements 115 having a common form and one or more fiducial or reference elements 116 having a reference form that is different than the common form. As used herein, the term "form", when applied to an element or object, means a shape and orientation of the element or object, without regard to its scale or dimension. As used herein the term "different", when applied to a comparison between two or more "forms", means the forms being compared have a different shape and/or orientation in comparison to one another. As used herein the term "same", when applied to a comparison between two or more "forms", means the forms being compared have equivalent shape and/or orientation in comparison to one another.

With additional reference to FIG. 2A, in certain embodiments, the pattern 108 may additionally comprise a plurality of inner elements 117 that are disposed close to the aperture 112. In addition to being used to provide shape or profile information for the surface 102, the inner elements 117 may also be used in combination with a Helmholtz source, discussed below herein, to provide information regarding a location of the object 105 or surface 102 relative to the system 100. The inner elements 117 may have the same form as the common elements 115. Alternatively, the form of elements 117 may be different from that of elements 115, for example, having the same shape, but having a smaller diameter. The pattern 108 may also include additional light sources 118 that are not generally used to determine a surface 102 shape, but may be used for other purpose, for example, as light sources to illuminate the object 105 to obtain an image of the surface 102, or to control a pupil size, when the object 105 is an eye of a living mammalian subject.

In general, the pattern 108 and the associated plurality of first elements 110 may be consider a Placido-type source. As used herein, the term "Placido-type source" means a mask, pattern, or plurality of individual light sources disposed such that light from the source reflects off of a reference or test object, passes through an imaging system, and is received by a detector, wherein light from the Placido-type source passes only once through the imaging system. The individual light sources may be active sources generating light energy or apertures through which light energy is transmitted. Individual mask or pattern features may include lighter or more reflective portions of the mask or pattern configured to reflect light. As used herein, the terms "Placido disk" means a Placido-type source configured as a plurality of concentric rings or annular shapes. As used herein, the term "Placido system" means a system for making surface measurements using a Placido disk or Placido-type source, which may include an imaging optic or system, detector or detector array for receiving images of the source, and processor for collecting and using image data to calculate a test surface shape.

The common elements 115 in the illustrated embodiment are in the form of circular disk, preferably having a diameter of less than 2 mm or less than 1 mm. In some embodiments, the circular disk is sufficiently small to be, or to approximate, a point source of light. The reference elements 116 are in the form of crosses in the illustrated embodiment, preferably having a characteristic diameter or dimension that is less than a nominal spacing between the common elements 115, for example, less than 50% of a nominal spacing between the common elements 115 or less than 25% of a nominal spacing between the common elements 115. Alternatively, the characteristic diameter or dimension of the reference elements 116 may be relatively large, so that they may be easily identified, for example, on the order of a nominal spacing between the common elements 115 or even larger than a nominal spacing between the common elements 115. Other shapes of the reference elements may be preferred in certain situations, for example, in the form of an oval, an "x", or a polygon, such as a triangle or a rectangle.

The illustrated embodiment shows four reference elements 116, with pairs of elements 116 disposed along orthogonal axes (e.g., two elements 116 along a horizontal axis and two elements 116 along a vertical axis). Four reference elements 116 may have an advantage that their images may be used to determine an astigmatism of the test object 105 or of the optical system 122. In some embodiments, the pattern 108 may include more than four or less than four reference elements 116. For example, more reference elements 116 (e.g., 8, 12, 16, or more than 16 reference elements) can be beneficially incorporated in applications where the test object 105 is expected to be very complex or have many areas with large slope gradients. In such circumstances, an increased number of reference elements can aid in mapping and correlating individual common elements 105 to their corresponding images at a detector.

Each of the common elements 115 and/or each of the reference elements 116 may have the same shape, size and orientation, as illustrated in FIG. 2. Alternatively, one or more of the common elements 115 may have a different size, shape, or orientation than the other common elements 115. Similarly, one or more of the reference elements 116 may have a different size, shape, or orientation than the other reference elements 116, for example, to further aid in mapping or correlating individual first elements 110 to their corresponding images at a detector.

Referring again to FIG. 1, and with additional reference to FIG. 3, the system 100 also includes a detector array 120 and an optical system 122 that is configured to provide a spot image 123 of the plurality of first elements 110 when light therefrom: reflects off the surface 102 of a test object 105, passes through the aperture 112, and is received by the detector array 120. The spot image 123 comprises a plurality of individual images or spots 123a that are produced from corresponding elements of the plurality of first elements 110. As used herein the term "spot", when used in the context of the content of an image captured by a detector array, means one or more pixels of the detector array that may be associated with an external signal or object, for example as a result of having pixel signals that are generally higher than that of neighboring pixels outside the spot. The spot may be associated with a size and/or shape, which may be indicative of information related to the external signal producing the spot, for example, a position of the spot, an amount of defocus of an image, an aberration of an image such as coma, and the like. For embodiments of the current invention, the shape of a spot may be indicative of the shape of a corresponding element or light source producing the spot and, therefore, indicative of the identity and/or location of the element or light source, or of a characteristic of an intermediate object or optical element within an optical path.

The system 100 also includes processor 124, including an electronically readable memory containing data and/or instructions. The processor 124 may be configured to control the system 100, for example, to operate active elements such as detectors and light sources of the system 100. The processor may additionally be configured to collect and/or analyze data provided by the system 100.

The system 100 is generally configured to map at least some of the first elements 110 to an image space located at or near the detector array 120, whereby the spot image 123 is representative of the mapped image of first elements 110. The detector array 120 may be any suitable electronic device for recording an image, for example, a charge-coupled device (CCD) array, a charge injection device (CID) array, or the like. Because light from the first elements 110 is reflected off the surface 102, the surface 102 may be considered to form a virtual image of the first elements, whereby the content of the virtual image (shape, size, magnification, aberrations, distortions, and the like), as recorded by the detector array 120, is affected by the shape of the surface 102. Accordingly, the spot image 123 generally contains information or data that may be used to analyze the surface 102 to determine its physical characteristics (e.g., shape, size, or orientation) and/or optical characteristics (e.g., radius of curvature, focal length, asphericity, aberrations such as astigmatism or spherical aberrations, and the like).

The test object 105 may be any object comprising a surface 102 that is generally specularly reflective of incident light or radiation from the first elements 110. The surface 102 may be a reference surface, for example, to calibrate, certify, and/or align the system 100. A reference surface 102 may, for example, have a spherical shape having a predetermined radius of curvature, or have an aspheric shape having predetermined characteristics (e.g, a conic section characterized by a curvature and a conic constant, or additionally or alternatively by higher order polynomial terms such as Taylor series coefficients or Zernike coefficients). Because the surface 102 of the test object 105 is disposed along an optical path between the first elements 110 and the detector array 120, the shape of the surface 102 will affect the resulting image of the first elements 110 in a way that may allow the surface 102 to be reconstructed (e.g., by comparison to a reference surface having a known geometry).

With continued reference to FIG. 3, the spot image 123 generally includes a plurality of common spots or images 125, produced by at least some of the plurality of common elements 115, and one or more fiducial or reference spots or images 126, produced by at least some of the fiducial or reference elements 116. The common spots 125 may also be considered to include spots 127 that are produced by the inner elements 117. In certain embodiments the inner spots 127 have a same shape and/or orientation as the common spots 125 of the common elements 115, but have a different size, for example, to aid in mapping each of the first elements 110 to their corresponding spot image 123. Alternatively, spots 127 may have the same shape, size, and orientation as the common spots 125.

Because of their distinct and different shape, and/or because of their relatively few numbers, the reference spots 126 are advantageously easy to associate with their corresponding reference elements 116. The inventors have found that the reference spots 126 may be used to great advantage to correlate the each of the common spots 125 with their corresponding common elements 115. This has been found to be of particular importance when the surface 102 of the test object 105 has a three dimensional profile that is relatively complex (e.g., with large gradients or deviations form a relatively simple surface like spherical surface). In addition, the reference spots 126 may be used to obtain other information about the system 100 and/or test object 105, for example, the location of the object 105 or surface 102 relative to an assumed or ideal position, distortions in the optical system 122, misalignment of the plurality of the first elements 110 with the system 100, general astigmatism in the surface 102, and the like.

In the illustrated embodiment shown in FIG. 2, the pattern 108 comprises a plurality of individual light sources disposed on a surface. Alternatively, the pattern 108 may comprise an opaque mask containing a plurality of apertures or openings that allow light from behind the mask to be transmitted to, and reflected off, the surface 102. In yet other embodiment, the pattern 108 comprises a mask in which the first elements 110 are in the form of lighter colored, more highly reflective, or more specularly reflective areas of the mask.

The optical system 122 may include a pair of lenses 130 and 132 that are configured to produce an image of the first elements 110 on or near the detector 120. The lenses 130, 132 may be refractive lenses or, alternatively, be reflective or diffractive optical elements. The optical system may also includes an aperture 135 that is configured to block unwanted rays of the first elements 110 from reaching the detector array 120. Other optical configurations incorporating other optical elements such as additional focusing elements, beamsplitters, spectral filters, polarizing filters, waveplates, and the like are anticipated, especially when the system 100 is integrated with other optical systems, as discussed below herein.

Figure 4:
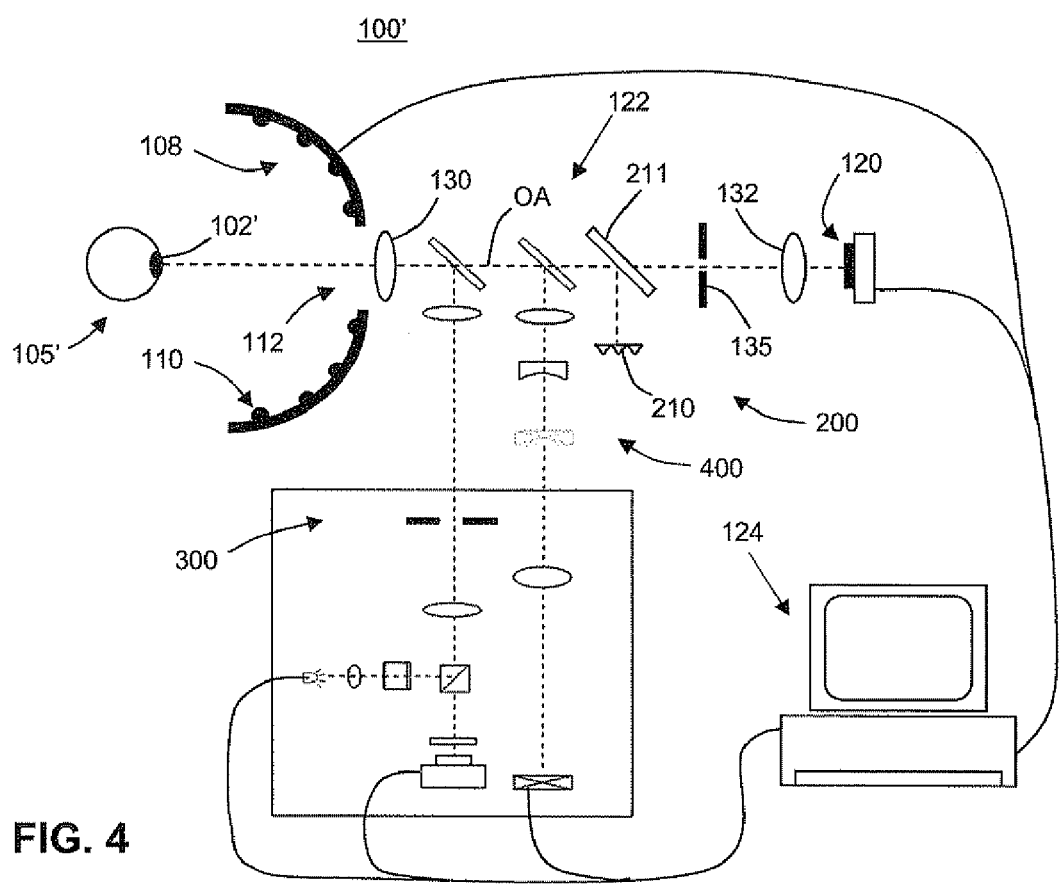
FIG. 4 is a schematic drawing of a measurement system according to another embodiment of the present invention.

Referring to FIG. 4, in certain embodiments, the system 100 is an ophthalmic system 100' that is used to determine optical and/or physical characteristics of a test eye 105' having a corneal surface 102'. The test eye 105' may be that of a live human subject or an animal subject such as a mammal, bird, reptile, or the like (e.g., for use in animal trials for development of ophthalmic devices or procedures). Alternatively, the test eye 105' may be a model eye configured to simulate the shape of a mammalian eye, or a reference object used to calibrate or align the ophthalmic system 100'. As compared to the system 100 shown in FIG. 1, the system 100' may additionally comprise a Helmholtz source 200, a wavefront analyzer 300, and/or a target system 400, for example, to control the accommodative state of the eye 105'. It will be appreciated that as configured, the system 100' or subsystems thereof may also be used to obtain optical and/or physical characteristics of other objects besides an eye, for example, an optical lens, a contact lens, an intraocular lens (IOL), or the like. The system 100' is similar to, and performs similar functions to, those discussed in U.S. patent application Ser. No. 12/347,909, which is herein incorporated in its entirety for all purposes as if fully set forth herein. The system 100' may also include other subsystems, for example, a tomographer such as an OCT (not shown).

The wavefront analyzer 300 may be based on interferometric systems, Shack-Hartmann wavefront sensors, or the like. Suitable Shack-Hartmann wavefront sensors are disclosed, for example, in U.S. Pat. Nos. 6,550,917 (Neal et al.), 6,130,419 (Neal), 6,052,180 (Neal et al.), or 5,777,718 (Williams et al.), all of which are hereby incorporated by reference in their entirety for all purposes as if fully set forth herein. A tomographer based on a Shack-Hartmann wavefront sensor may also be incorporated into the system 100', for example, as disclosed in U.S. Pat. No. 6,634,750, which is hereby incorporated by reference in its entirety for all purposes as if fully set forth herein.

The Helmholtz source 200 comprises a plurality of second elements or light sources 210 that are preferably optically located at a distance from the lens 130 that is equal to one focal length, or about one focal length, of the lens 130. The second light sources 210 are configured to reflect light off a beamsplitter 211, and then to transmit the reflected light through the lens 130 and aperture 112, then off the surface 102', then back a second time through the aperture 112, and finally received by the detector array 120. The second elements 210 may comprise a plurality of individual light sources (e.g., LED light sources), a plurality of apertures in an opaque mask that is illuminated from behind the mask, or the like.

As used herein, the term "Helmholtz source" or "Helmholtz light source" means one or a plurality of individual sources or individual light sources disposed such that light from each of the individual light sources passes through an optical element having optical power, reflects off of a test object, passes through the optical element, and is received by a detector, wherein light from the Helmholtz source may be used to determine geometric and/or optical information of at least a portion of a surface of the test object. In general, it is a characteristic of Helmholtz sources that the signal at the detector is independent of the position of the test object relative to the Helmholtz source.

As used herein the term "light source" means a source of electromagnetic radiation, particularly a source in or near the visible band of the electromagnetic spectrum, for example, in the infrared, near infrared, or ultraviolet bands of the electromagnetic radiation. As used herein, the term "light" may be extended to mean electromagnetic radiation in or near the visible band of the electromagnetic spectrum, for example, in the infrared, near infrared, or ultraviolet bands of the electromagnetic radiation, or to mean electromagnetic radiation detectible by a photodetector or electromagnetic image sensor (e.g., CCD) or that is useful in measuring the optical or physical characteristics of an object under examination.

Figure 5:
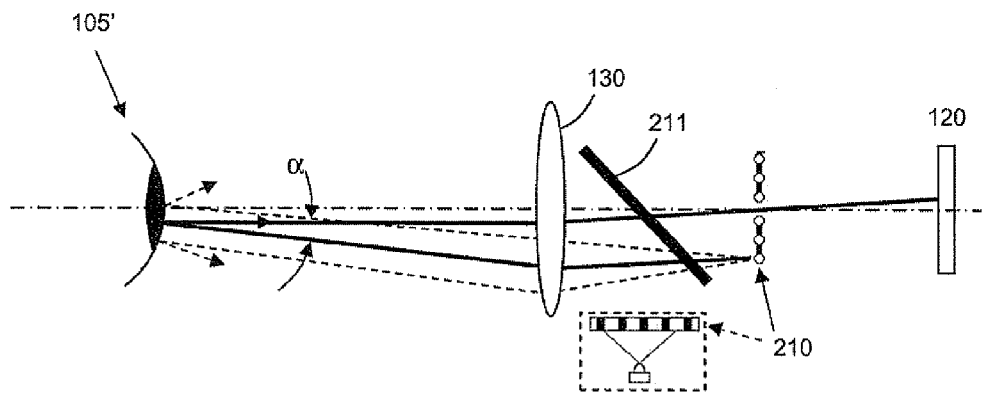
FIG. 5 is a magnified view of a portion of the system shown in FIG. 4.

The beamsplitter 211 may be configured to virtually locate the second elements in the same plane as the aperture 135. As illustrated in FIG. 5 and discussed further in the U.S. application Ser. No. 12/347,909, each of the second elements 210 is configured to produce a collimated beam of light that is reflected off the corneal surface 102' at a known point that is independent of the location of the surface from the system 100'. Advantageously, the second elements 210 may be used to obtain topography information of the central or paraxial portions of the surface 102' that are not attainable with the first elements 110 due to the presence of the aperture 112. The second elements 210 may also be used in combination with the inner elements 117 to determine a distance of the surface 102' from the system 100'.

Figure 6:
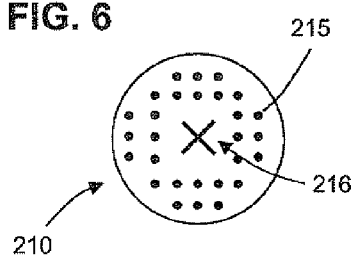
FIG. 6 is a magnified view of a second pattern of elements of the system shown in FIG. 4.
Figure 7:
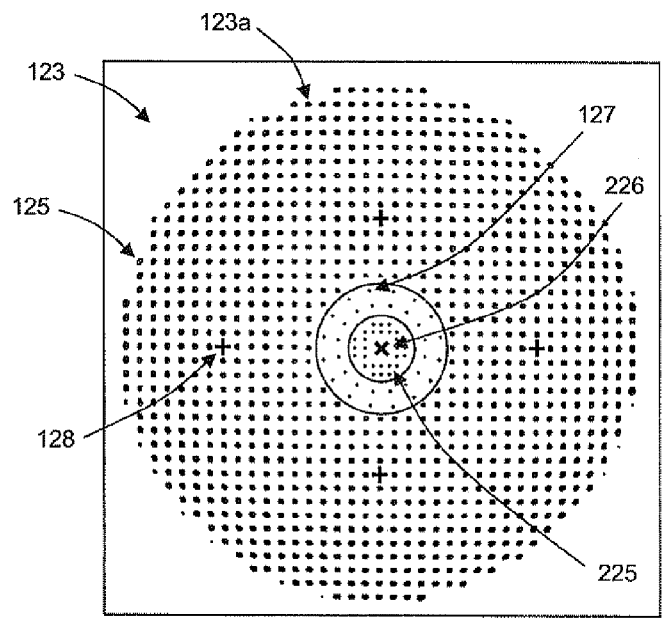
FIG. 7 is a view of an image produced of first and second pattern of elements of the system shown in FIG. 5.

Referring to FIG. 6, the second elements or light sources 210 of the Helmholtz source 200 comprises a plurality of Helmholtz common elements 215 having a common form and a Helmholtz fiducial elements or reference element 216 having a reference form that is different than the common form. Referring to FIG. 7, the Helmholtz elements 215, 216 produce at the detector array 120, respectively, a plurality of Helmholtz common spots 225 and one or more fiducial or reference spots 226 (one spot 226 being illustrated in FIG. 6). Accordingly, the spot image 123 and the individual images or spots 123a may additionally include the spots 225, 226, as well as the spots 125, 126, 127 produced by images of the plurality of the first elements 110. As illustrated in FIGS. 6 and 7, the reference element 216 may have a form that is different from that of any or all of the forms for the elements 115, 116, 117, and/or 215. The Helmholtz reference element 216 in the illustrated embodiment is disposed along the central axis OA of the system 100'.

The plane of the Helmholtz source 210 may be located optically at a know position. Accordingly, it may be advantageous that a series of reference measurements be used to locate and set this position. To this end, a calibration object can be placed where the test object or eye 105, 105' would normally go, so as to determine the correct position of the Helmholtz source. This may be done by placing an element with a known (or even just fixed) radius of curvature at position of 105, 105', and then varying the position relative to lens 120 in a known manner. The objective is to place the Helmholtz source at a position such that the received Helmholtz source pattern is independent of the relative position. Accordingly, the source 210 may be positioned so that there will be no dependence on the position of then object 105, 105'. The source 210 position can be adjusted with shims or other method until a desired result is obtained.

Image data obtained from the systems 100 or 100' may be analyzed—for example, using the processor 124 or an external processor not shown—to provide information regarding the shape of a surface of the test object 105 or the test eye 105'. The resulting information regarding a surface profile of a test object surface 102 may be used to correct a defect of the object 105 or to reject the object 105 if the surface defect is not repairable or is too expensive to repair. When the systems 100 or 100' are used in ophthalmic applications, a measured shape of a corneal surface and/or aberrations of the eye (e.g., using the wavefront analyzer 300) may be obtained and used to correct visions. For example, analyzed data from the systems 100 or 100' may be used in conjunction with a corneal refractive procedure such as a LASIK or PRK procedure. In certain embodiments, output from the systems 100 or 100' may be used in determining a treatment plan for operating a laser for providing the refractive procedure.

In certain embodiments, a method 500 for measuring an object using the system 100, 100' includes the following modules:

Module 505: Provide a plurality of elements from a measurement system source.

Module 510: Reflect light from the elements off a surface of a test object.

Module 515: Create a plurality of images at a detector corresponding to the plurality of elements.

Module 520: Compensate or correct for optical aberrations, distortion, or misalignment of the system.

Module 525: Classify the images.

Module 530: Rank the images according to a criterion and select a subset of images based on a quality criterion.

Module 535: Associate the selected images with their corresponding source elements.

Module 540: Determine or estimate a shape or local slopes of the test object base on the selected images.

Figure 8:
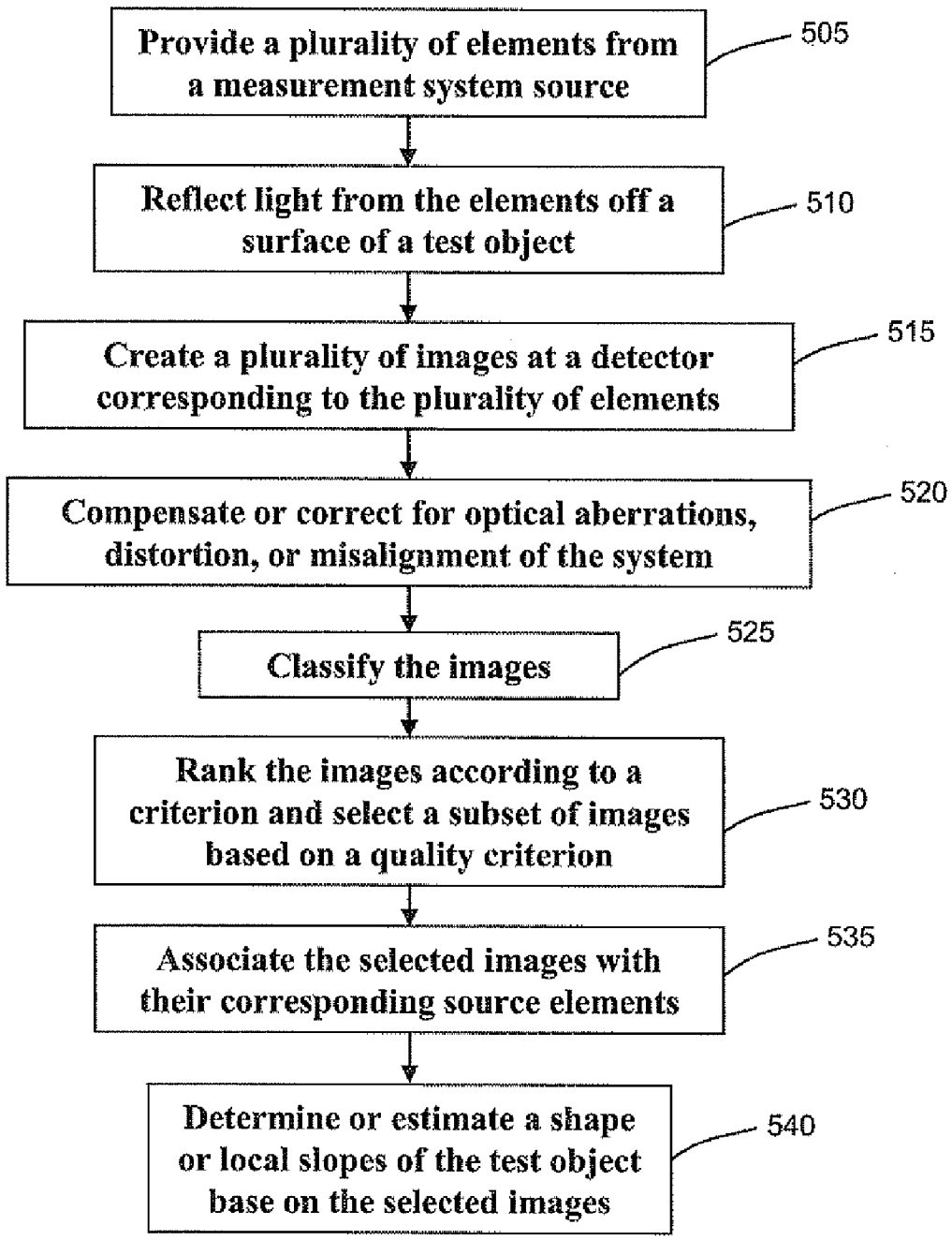
FIG. 8 is a flow chart showing a method for measuring an object according to an embodiment of the present invention.

In some embodiments, some of the modules of the method 500 may be excluded or performed in a different order than indicted by the flow diagram in FIG. 8. Generally, some or all of the modules of the method 500 may be incorporated into the processor 124.

Module 505 may comprise only using the plurality of first elements 110 from the systems 100, 100', generally using all elements 115, 116, 117. Alternatively, module 505 may additionally comprise using the second elements or light sources 210 of the Helmholtz source 200, including common elements 215 and reference element 216.

Module 510 may include reflecting light from first and/or second elements 110, 210 off surface 102, 102', whereby reflected light passing through the aperture 135 is imaged by the detector 120 in module 515. With reference to FIG. 3, module 515 includes producing the spots 125, 126 and/or 127 of the plurality of first elements 110. With additional reference to FIG. 7, module 515 may additionally include producing spots 225 and 226 of the plurality of second elements 210.

Module 520 may comprise compensating or correcting for aberrations or distortions in the system 100 or 100', particularly the optical system 122. Module 520 may also includes compensating or correcting for misalignment of various elements or sub-systems of the system 100, 100', for example, the lenses 130, 132 or the overall alignment or location of the plurality of first elements 110 or the plurality of second elements 210. The inventors have determined that topography systems based on reflected images off a test object can be extremely sensitive to such aberrations, distortions, or systems misalignments, especially when the test object is relatively complex and/or when high resolution profiling is desired. The inventors have further found a dramatic and unexpected increase in the quality of the surface profiling of a test object may be obtained when such aberrations, distortions, or systems misalignments are taken into account. Thus, profiling or topography systems according to embodiments of the present invention have been found to provide improved accuracy and/or higher resolution or dynamic range.

In certain embodiments, system aberrations, distortions, and/or misalignment are determined by modeling all or portions of the system 100 or optical system 122, for example, by using optical modeling or ray tracing software, such as ZEMAX® marketed by ZEMAX Development Corporation, 3001 112th Avenue NE, Suite 202, Bellevue, Wash. 98004-8017 USA (www.zemax.com). Alternatively or additionally, system aberrations, distortions, and/or misalignment may be determined by direct measurement of all or portions of the system 100 or optical system 122. For example, a wavefront sensor, such as Shack-Hartmann wavefront sensor, may be located at or near a plane of the detector 120 or test surface 102, 102' and a collimated wavefront propagated through the optical system 122. Alternatively or additionally, system aberrations, distortions, and/or misalignment may be determined by placing a reference surface at the predetermined location relative to the measurement system 100 (e.g., in a plane of the test object 100, 100') and reflecting light from the plurality of first and/or second elements 110, 210 off the reference surface. Such measurement could alternatively be made by replacing the first and/or second elements 110, 210 with a calibration fixture and reflecting light from the calibration fixture off the reference surface.

Figure 9:
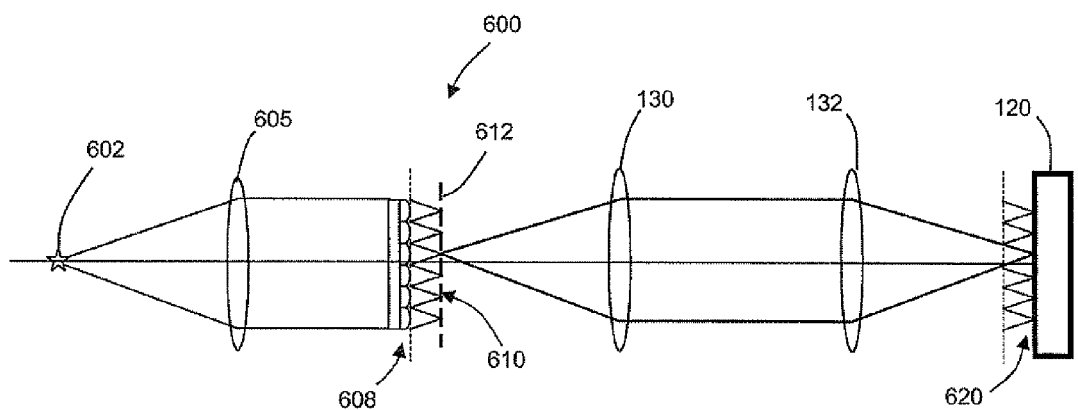
FIG. 9 is a schematic drawing of calibration system according to an embodiment of the present invention for measuring distortions of an optical system.

Referring to FIG. 9, a calibration system 600 for determining distortions of the lenses 130, 132 of the optical system 122 of the system 100, 100' is illustrated. The system 600 comprises a plurality of point sources 612 that may be produced by a point source 602, a collimating lens 605 located a focal length away from the point source 602, and a lenslet array 608. The point sources 610 are generally disposed along a plane 612. Light from each of the point sources 610 propagates through the lenses 130, 132 and is refocused again at the detector array 120. Light from one of the point sources 612 is shown propagating through the lenses for illustrative purposes. In similar fashion each of the point sources 612 propagate through the lenses 130, 132 to produce a plurality of imaged point sources 620 disposed along the face of the detector array 120. Distortion produced by the lenses 130, 132 of the system 100 may be determined by measuring coordinates on the detector array 120 of each of the imaged point sources 620.

Based on the above or similar methods or systems, the aberrations, distortions, or misalignment of a system may be directly measured and subsequently converted into appropriate calibration data, for example, as a lookup table or set of parameter, such as a set of polynomial coefficients.

The calibration data may be used in various ways to correct or compensate for system aberrations, distortions, or misalignment. For example, in certain embodiments, locations or coordinates within the detector array 120 or overall image thereof is calculated for individual images of some or all of the elements of the plurality of first and/or second elements 110, 210. Thereafter, the calibration data may be used to recalculate the location or coordinate for the individual images. This corrected coordinate data may then be further processed to determine or calculate a shape or profile of the object 102, 102'. Alternatively, a shape or profile of the object 102, 102' may first be determined or calculated based on raw data contained in the overall image captured by the detector array 120 of the images of the plurality of first and/or second elements 110, 210. Subsequently, corrections to the shape/profile calculations may be made based on the calibration data. Other methodologies for utilizing the calibration data are anticipated.

Experiments were conducted to demonstrate the benefits and advantages of correcting for distortion in the lenses 130, 132 of the optical system 122. First, optical system distortions were measured using the calibration system 600 illustrated in FIG. 9. Next, three different spherical test objects 105, having radius of curvatures of 7.1412 mm, 7.9312 mm, and 8.7287 mm, respectively, were each analyzed using the pluralities of first and second light sources 110, 210. For each test sphere 105, image data was collected for varying amounts of known misalignment of the test sphere 105 to the system 100'. Measuring spheres of different radii and at different amounts of misalignment showed a trend in the elevation data that was due to distortion in the optical system.

The three test spheres 105 were individually mounted on an x-y-z translation stage and measurements were made at different x, y, and z locations, with x being a horizontal axis, y being a vertical axis, and z being along the system optical axis OA. In this way, the effects of misalignment on the instrument accuracy were determined. The metric used to evaluate accuracy was an elevation Peak-to-Valley (PV). The elevation PV was defined as the maximum surface error minus the minimum surface error, after removing a best fit spherical surface from the reconstructed surface 102. For an aligned sphere and no optical system aberrations or distortions, the error surface would be expected to be flat (all zeros); however, due to measurement noise etc. an elevation error in the micron range was observed.

Data for each of the three test spheres 105 was obtained for misalignments along the x-axis of 0 mm (i.e., on-axis or no misalignment), 0.64 mm, 1.27 mm, and 1.9 mm. The average PV error for various measurements made for each of the conditions tested is shown in Table 1 (without correction for measured distortion of lenses 130, 132) and in Table 2 (with correction for measured distortion of lenses 130, 132).

TABLE 1

Average PV errors in um (data uncorrected for optical system distortion).

| Misalignment | Sphere radius | | |
|---|---|---|---|
| (mm) | 7.14 mm | 7.93 mm | 8.72 mm |
| 0 | 0.86 | 0.61 | 0.93 |
| 0.64 | 1.75 | 2.05 | 2.50 |
| 1.27 | 3.09 | 3.65 | 4.57 |
| 1.90 | 5.32 | 6.14 | 6.75 |

TABLE 2

| Misalignment | Average PV errors in um (data corrected for optical system distortion). Sphere radius | | |
|---|---|---|---|
| (mm) | 7.14 mm | 7.93 mm | 8.72 mm |
| 0 | 0.60 | 0.32 | 0.46 |
| 0.64 | 1.14 | 0.84 | 1.59 |
| 1.27 | 0.92 | 1.10 | 1.37 |
| 1.90 | 1.62 | 1.60 | 1.76 |

As can be seen from these results, PV error is significantly decreased when corrected for distortion of the lenses 130, 132, especially as the misalignment of the test spheres 105 are increased.

The methods described herein relating to compensation or correction of system aberrations, distortions, or misalignment have been particularly illustrated for topography systems. However, it will be appreciated that such methods may be additionally applied to other optical systems where complex mappings between an object space and an image space are sensitive to system aberrations, distortions, or misalignment. For example, system compensation or correction methods according to embodiments of the present invention may also be applied to wavefront sensors application or other applications where a large number of data points are analyzed in measurement image.

Module 525 may comprise classifying the individual images of the spots 125, 126, 127, 225, and/or 226. For example, the individual images may be classified as belonging to the common or reference elements of the plurality of first or second elements 110, 210 and/or as belonging to the plurality of first elements 110 or belonging to the plurality of second elements 210. The individual images may be further classified or sub-classified, for example, according to which of the four reference elements 116 in FIG. 2 they are associated with or belong to. Additionally, the common spots 125, 127 may be classified as belonging to either common elements 115 or the inner elements 117.

Module 530 may comprise ranking the spots 125, 126, 127, 225, and/or 226 according their quality and selecting only those images that have a quality that is above a predetermined minimum. The inventors have found that use of poor quality image data elements can produce poor results when using the data to reconstruct a surface of a test object. For example, an ill formed image or spot of an individual common element 115, 215 may make it difficult or impossible to accurately calculate a coordinate for that individual element. Accordingly, it may be produce erroneous result when trying to reconstruct the local surface area or even to determine which element the individual image is associated with. In such cases it may be better to either eliminate the individual image or assign it a lower weighting when it is used to reconstruct the surface.

In certain embodiments, a quality value or index is assigned to each of the spots 123a of the spot image 123 (e.g., the spots 123a shown in FIG. 3 or 7) based on a predetermined criterion for evaluating the quality of each image or spot (e.g., spot shape, number of pixels in a spot, distribution of pixels of a spot, variation of intensity of pixels within a spot, etc.). Each spot 123a having a quality value above a predetermined threshold value may be selected for further processing. Additionally or alternatively, certain spots 123a may be assigned a weighting or weight value, depending on their quality value. During later processing (e.g., within the association module 535 and/or the shape determination module 540) the weighting of a spot 123a may be used to determine how it will used relative to other neighboring spots 123a.

In certain embodiments, one or more of the spots 123a are evaluated for quality using two or more different criteria, algorithms, or methods. The results from each criteria, algorithm, or method may then be compared with one another to determine whether to accept or reject the one or more spots 123a, or to determining a weighting or weight value for each of the one or more spots 123a. In addition, results from one of the criteria, algorithms, or methods may be evaluated in light of the other two or more different criteria, algorithms, or methods. In this way, it can be determined whether the results from the evaluated criteria, algorithm, or method are valid and/or whether results from the evaluated criteria, algorithm, or method should be used to evaluate a particular spot 123a or set of spots 123a.

Module 535 may comprise one or more methods for associating each of the spots 123a with a corresponding element from the plurality of first and/or second elements 110, 210. The fiducial or reference spots 126 and/or 226 can provide an overall estimate of a regional or global average spot grid spacing or separation. Since the fiducial or reference spots 126, 226 have a different shape than the common spots 125, 127, 225, they are easily associated with their corresponding elements from the first and second elements 110, 210. Thus, reference spots 126 and/or 226 are easily associated with their corresponding reference elements 116, 216 and advantageously provide starting points for associating neighboring common spots 125, 127, and/or 225 with their corresponding common elements 115, 117, and/or 215. Accordingly, one or more of the reference spots 126, 226 may be used in an iterative extrapolation method that spirals out, starting at the reference spot location, progressing outwards to include a first plurality of neighboring common spots, then adding other pluralities of neighboring common spots of the first plurality of neighboring common spots. One method of associating the common spots 125, 127, and/or 225 with their corresponding common elements 115, 117, and/or 215 includes:

1. Calculate coordinates for a fiducial or reference spot 126 or 226.
2. Associate the reference spot 126 or 226 with its corresponding element 116, 216.
3. Identify and calculate coordinates for a first plurality of neighboring common spots 125, 127, and/or 225 located near, adjacent, or proximate the reference spot 126, 226.
4. Optionally eliminate image spots on detector 120 that are determined not to come from an element 115, 117, 215.
5. Associate the first plurality of neighboring common spots 125, 127, and/or 225 with their corresponding elements 115, 117, 215.
6. Identify and calculate coordinates for a second plurality of neighboring common spots 125, 127, and/or 225 located near, adjacent, or proximate the spot of the first plurality of neighboring common spots 125, 127, and/or 225.
7. Optionally eliminate image spots on detector 120 that are determined not to come from an element 115, 117, 215.
8. Eliminate, or refine calculations for, redundantly identified common spots 125, 127, and/or 225.
9. Repeat items 2-8 for additional pluralities of neighboring common spots 125, 127, and/or 225 until a predetermined criteria is met.

10. Repeat items 1-9 for all other reference spots 126 or 226 or a predetermined number of reference spots 126 or 226

11. Eliminate, or refine calculations for, redundantly identified common spots 125, 127, and/or 225 found in item 10.

Using the above or a similar method, each iteration may include a neighborhood of spots that are further and further away from the starting reference spot 126, 226. A local polynomial fit or other algorithm may also be employed, whereby a grid position may be assigned to each spot, extra spots that do not fit into the grid pattern may be eliminated, and/or missing elements 110, 210 may be ascertained. In addition, reference spots 126 and/or 226 may be used to determine an expected global or regional average spacings between common spots 125, 127, and/or 225, which can be used in items 3 and 6 of the above method help identify neighboring common spot, in items 4 and 7 aid in eliminating image spots on detector 120, and/or element 8 to aid in handling redundantly identified common spots. Additionally, the above method may also include accounting for missing spots. For example, in the case of a topographer for ophthalmic applications, some of the plurality of first or second elements 110, 210.

Additionally or alternatively to the above method, inner common spots 127 may be sorted by radius and angle in order to uniquely associate them with a corresponding inner element 117. Spots 225, 226 from the Helmholtz source 200 are generally well behaved and will generally lie almost exactly on a rectilinear grid. Thus, it may be unnecessary to use the above method for spots 225, 226, since they can be uniquely sorted/associated using a low order polynomial fit that checks the residual value for each spot in order to eliminate spots that are not well behaved within the rectilinear grid.

Figure 10:
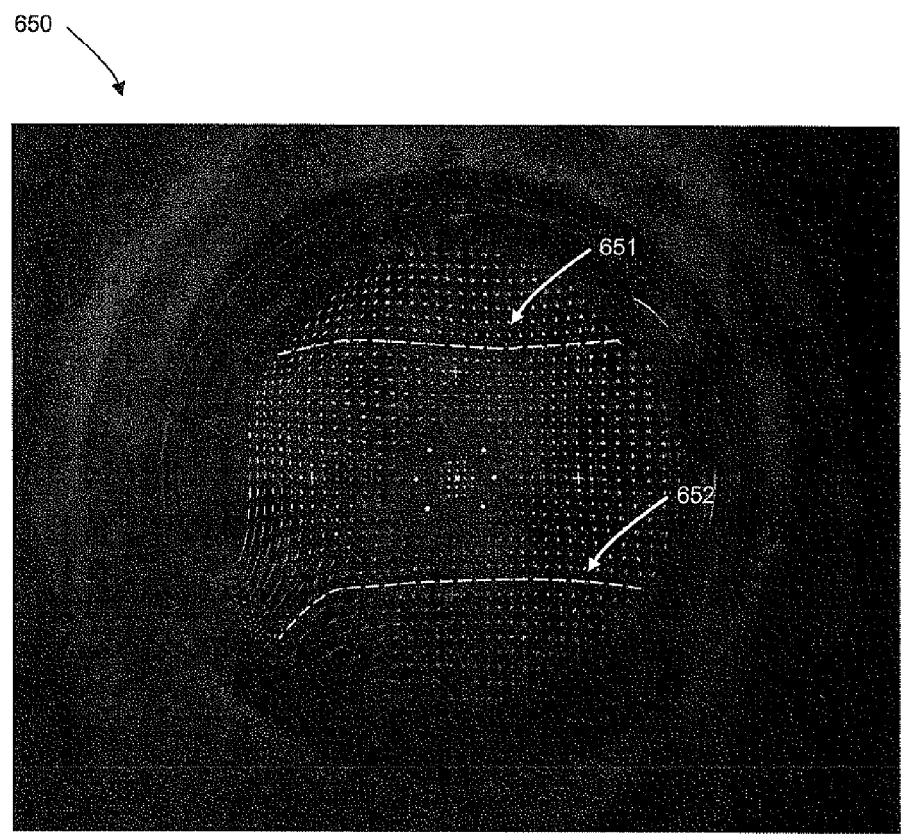
FIG. 10 is an output of a system according to an embodiment of the present invention showing an image of a model cornea configured to simulate keratoconus.

Referring to FIG. 10, an image 650 is shown of a model cornea configured to simulate keratoconus. The image was produced using a system similar to the system 110, in FIG. 4, with the image being produced from light sources equivalent to the first and second plurality of elements 110, 210. Image spots 125, 126, 127, 225, and 226 are clearly shown. Dotted lines 651, 652 show examples of sets of common spots that were successfully associated with their corresponding common elements or light sources, thus allow the shape of the model cornea to be successfully obtained.

Figure 11:
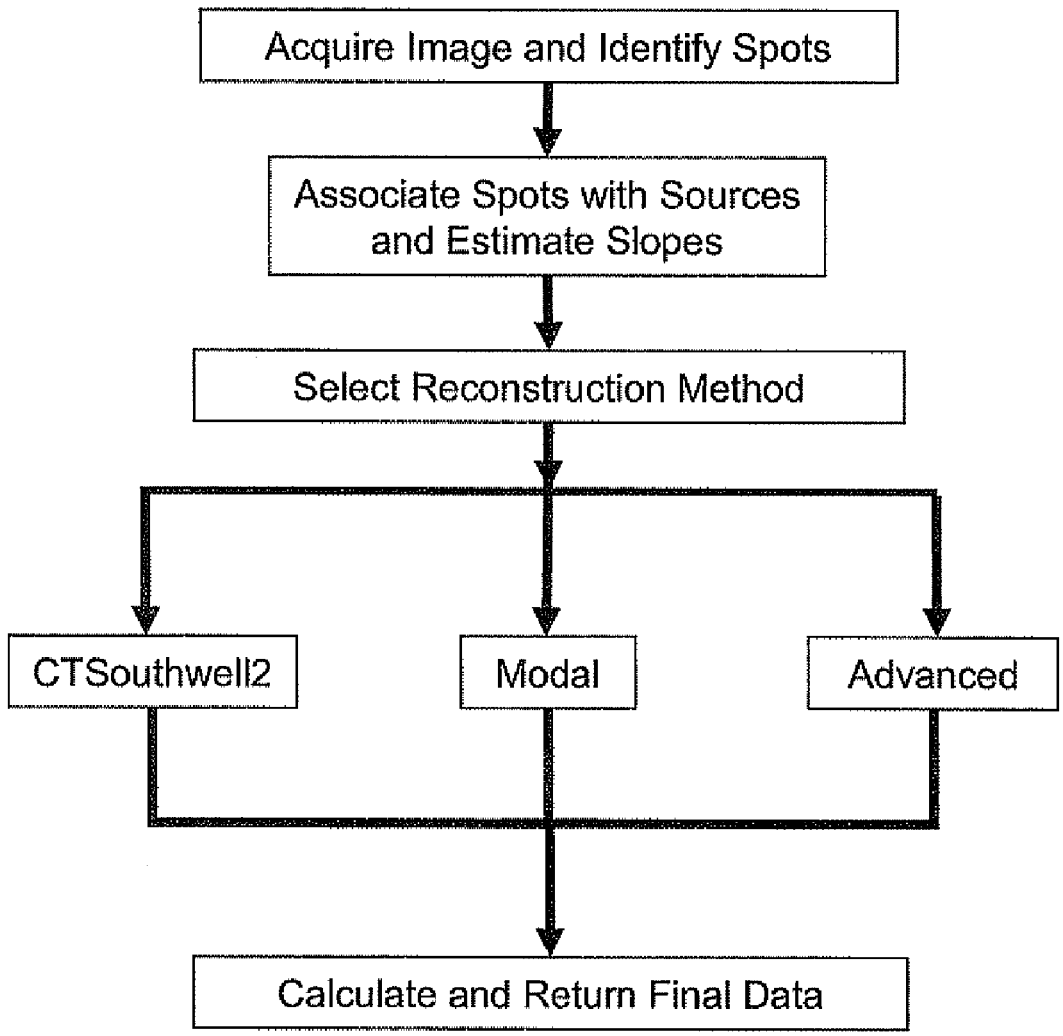
FIG. 11 is a flow chart showing a method for reconstructing at least one surface portion of the surface according to an embodiment of the present invention.

Module 540 may comprise determining or estimating the shape or local slopes of the a corneal surface 102' based on spots 125, 126, 127, 225, and 226 after being processed per modules 520-535. Referring to the flowchart in FIG. 11, a method 700 for reconstructing at least one surface portion of the corneal surface 102' is shown. As discussed above, the process begins with the acquisition of the raw images and identification of the individual images of spots 125, 126, 127, 225, and 226. A technician may position a patient's eye within a few millimeters of the nominal object plane, nominally centered in the field of view before acquiring the image. The inner and outer light sources 115, 116, 117 simultaneously illuminate the corneal surface 102' to obtain full coverage.

Once segregated into their respective sources, the pluralities of spots 125, 127, 128, 225, and 226 are associated with specific sources within each category as discussed in module 525. This information may be used to calculate the surface gradient at each image location. There are at least three reconstruction methods that may be used on the spots 125, 127, 128, 225, and 226. The Modal reconstructor fits the gradient data to a set of Zernike polynomials; the CT Southwell2 and the Advanced reconstructors both are zonal reconstructors. The CTSouthwell2 reconstructor works on gradient data measured on a more-or-less rectilinear grid while the Modal and Advanced reconstructors are able to reconstruct surface data from gradient measurements located on non-rectangular grids. The slope and/or surface data are used to calculate data such as, but not limited to, optical aberration coefficients, radius of curvature, power map, de-center, and the like.

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

What is claimed is:

1. A system for determining a surface shape of a test object, comprising:

a pattern including a plurality of first elements disposed about a central axis and defining an aperture containing the central axis, the first elements including a plurality of common elements having a common form and a reference element having a reference form that is different than the common form, the first elements further including a first reference element and a second reference element each having a same reference form that is different than the common form;

a detector array;

an optical system adapted to provide an image of the first elements when light reflects off a surface of a test object, passes through the aperture, and is received by the detector array; and a processor including an electronically readable memory, the electronically readable memory containing instructions to:

identify a plurality of element images on the detector array, each of the element images corresponding to the first reference element, the second reference element, or one of the plurality of common elements; and determine a surface shape of the test object based on locations of the element images on the detector array.

2. The system of claim 1, wherein the common form is a circular spot and the reference form is a cross, an "x" shape, or a polygon.

3. The system of claim 2, wherein the polygon is a triangle or a rectangle.

4. The system of claim 1, wherein the pattern is a mask containing the plurality of first elements.

5. The system of claim 1, wherein the plurality of first elements comprises a plurality of individual light sources.

6. The system of claim 5, wherein the plurality of individual light sources comprises a plurality of apertures in an opaque mask.

7. The system of claim 1, wherein system is an ophthalmic topographer and the test object is an eye of a mammalian subject or a model eye configured to simulate the shape of a mammalian eye.

8. The system of claim 7, wherein system further comprising one or more of a wavefront sensor, a Helmholtz source topographer, and optical coherence tomographer.

9. The system of claim 1, wherein the test object is a reference surface that comprises either a spherical shape having a predetermined radius of curvature or an aspheric surface of a predetermined shape.

10. The system of claim 1, wherein the electronically readable memory further includes instructions to classify each of the element images as corresponding to one of: a reference element of the first elements or a common element of the first elements.

11. The system of claim 10, wherein a classified reference element is further classified as corresponding to the first reference element or as corresponding to the second reference element.

12. The system of claim 1, wherein the electronically readable memory further includes instructions to assign a quality value to each of the element images and to select those element images having a quality value that is above a predetermined threshold value, the selected element images being used to determine the surface shape of the test object.

13. The system of claim 12, wherein the electronically readable memory further includes instructions to associate, by a function, at least some of the element images corresponding to common elements with an element image corresponding to the first reference element or the second reference element.

14. The system of claim 13, wherein the function is Taylor series.

15. The system of claim 1, wherein the first elements further includes a third reference element and a fourth reference element, wherein the first, second, third, and fourth reference elements all have a shared reference form that is different than the common forms.

16. The system of claim 1, wherein the electronically readable memory further includes instructions to determine an optical distortion of the system and to re-calculate locations for at least some of the element images based on the optical distortion.

17. The system of claim 16, wherein the electronically readable memory further includes distortion parameters used in re-calculating the locations of the at least some of the element images, the distortion parameters being in the form of an output from an optical model of the system.

18. The system of claim 16, wherein the electronically readable memory further includes distortion parameters used in re-calculating the locations of the at least some of the element images, the distortion parameters being in the form of calibration data of the system.

19. A system for determining a surface shape of a test object, comprising:
a pattern including a plurality of first elements disposed about a central axis and defining an aperture containing the central axis, the first elements including a plurality of common elements having a common form and a reference element having a reference form that is different than the common form, the first elements includes a first reference element and a second reference element each having a reference form that is different than the common form;
a detector array;
an optical system adapted to provide an image of the first elements when light reflects off a surface of a test object, passes through the aperture, and is received by the detector array; and
a Helmholtz source configured to transmit light through the aperture, then off the test object, then back through the aperture to be received by the detector array, the Helmholtz source comprising a plurality of Helmholtz common elements having a common form and a Helmholtz reference element having a reference form that is different than the common form of the Helmholtz source.

20. The system of claim 19, wherein the optical system includes an optical element having a focal length, f, and the Helmholtz source is located an optical distance of approximately of f away from the optical element.

21. The system of claim 19, wherein the detector array is configured to include an image of the Helmholtz reference element that is disposed along the central axis of the system.

22. The system of claim 19, wherein the detector array is configured to include a first image of the first elements and a second image of the Helmholtz reference element, the first image being disposed about the second image.

23. The system of claim 19, further comprising a processor including an electronically readable memory, the electronically readable memory containing instructions to:
identify a plurality of first element images on the detector array, each of the first element images corresponding to the first reference element, the second reference element, or one of the plurality of common elements of the first elements;
identify a plurality of second element images on the detector array, each of the second element images corresponding to the Helmholtz reference element or one of the plurality of common elements of the Helmholtz source;
determine a surface shape of the test object based on locations of the first element images and the second element images on the detector array; and
classify each of the element images as corresponding to one of: a reference element of the first elements, a Helmholtz reference element, or a common element of the first elements or of the Helmholtz common elements.

* * * * *